(12) United States Patent
Kong et al.

(10) Patent No.: US 7,136,155 B2
(45) Date of Patent: Nov. 14, 2006

(54) APPARATUS FOR MEASURING OIL OXIDATION USING FLUORESCENT LIGHT REFLECTED FROM OIL

(75) Inventors: Hosung Kong, Seoul (KR); Hung-Gu Han, Seoul (KR); Eui-Sung Yoon, Seoul (KR); Markova Lyubov, Gomel (BY); Nickolai Myshikin, Gomel (BY); Mikhail Semenyuk, Gomel (BY)

(73) Assignee: Korea Institute of Science and Technology, Seoul (KR)

( * ) Notice: Subject to any disclaimer, the term of this patent is extended or adjusted under 35 U.S.C. 154(b) by 361 days.

(21) Appl. No.: 10/837,972

(22) Filed: Apr. 30, 2004

(65) Prior Publication Data
US 2005/0088646 A1    Apr. 28, 2005

(30) Foreign Application Priority Data
Oct. 28, 2003    (KR) .................. 10-2003-0075404

(51) Int. Cl.
*G01N 33/28* (2006.01)
(52) U.S. Cl. ........................................ 356/70
(58) Field of Classification Search .................. 356/70, 356/317, 318, 436; 250/458.1, 459.1, 461.1
See application file for complete search history.

(56) References Cited

U.S. PATENT DOCUMENTS

| | | | | |
|---|---|---|---|---|
| 4,570,069 A | * | 2/1986 | Gager | 250/343 |
| 4,721,874 A | * | 1/1988 | Emmert | 310/333 |
| 5,049,742 A | * | 9/1991 | Hosonuma et al. | 250/301 |
| 5,200,027 A | * | 4/1993 | Lee et al. | 216/51 |
| 5,274,335 A | * | 12/1993 | Wang et al. | 324/689 |
| 5,929,754 A | * | 7/1999 | Park et al. | 340/439 |

OTHER PUBLICATIONS

ASTM International D92-05a, Standard Test Method for Flash and Fire Points by Cleveland Open Cup Tester, 2005.*
ASTM International D446-04, Standard Specifications and Operating Instructions for Glass Capillary Kinematic Viscometers, 2004.*
ASTM International D3524-90, Standard Test Method for Diesel Fuel Diluent in Used Diesel Engine Oils by Gas Chromatography, 1990.*
ASTM International D2272-02, Standard Test Method for Oxidation Stability of Steam Turbine Oils by Rotating Pressure Vessel, 2002.*
ASTM International D664-06, Standard Test Method for Acid Number of Petroleum Products by Potentiometric Titration, 2004.*
ASTM International D4739-05, Standard Test Method for Base Number Determination by Potentiometric Titration, 2005.*

* cited by examiner

*Primary Examiner*—Layla G. Lauchman
*Assistant Examiner*—David H. Parker
(74) *Attorney, Agent, or Firm*—Jones Day

(57) ABSTRACT

An apparatus for measuring oil oxidation is capable of being mounted to mechanical devices for detecting power of fluorescent light reflected from oil in real time as an indication of the oil oxidation. A plurality of first optical fibers are connected to a light-emitting member for introducing the light into oil at different incidence points. A plurality of light-reflecting mirrors are immersed in the oil and disposed opposite to the incidence points. The light-reflecting mirrors are located at different distances from the incidence points. A plurality of second optical fibers are connected to the incidence points, respectively. A plurality of light-receiving members are connected to the second optical fibers for receiving the light and outputting the signals corresponding to the received light. A control portion calculates a fluorescence quantum yield and a light absorption coefficient of the oil based upon the signals from the light-receiving members and compares them with the reference values pre-stored in the control portion to determine the oil oxidation.

9 Claims, 3 Drawing Sheets

APPARATUS FOR MEASURING OIL OXIDATION USING FLUORESCENT LIGHT REFLECTED FROM OIL

FIELD OF THE INVENTION

The present invention relates to an apparatus for measuring oil oxidation, and more particularly, to an apparatus for measuring oil oxidation capable of being mounted to mechanical devices for detecting the power of fluorescent light reflected from oil in real time as an indication of the oil oxidation.

BACKGROUND OF THE INVENTION

Generally, the life span of oil, e.g., used in the engine of a vehicle, depends on various conditions, such as the running distance of the vehicle, operating time of the engine, driving environment, and so on.

In most cases, because of physical and chemical degradations, the oil should be replaced regularly. The physical degradation of the oil is usually caused by metallic wear particles and dusts introduced into the oil from outside. These contaminants cause excessive wear on the surfaces of engine components, like cylinders, bearings, cylinder walls, and pistons, thereby deteriorating engine performance considerably. In addition, the chemical degradation is predominantly caused by moisture, degradation products, coolants and foreign oil types flowing into the oil.

There are a variety of methods for determining the condition of oils, but most of these techniques are based on debris monitoring and viscosity. These measurements provide insight into the physical changes that have occurred in the oil (i.e. the presence of metal debris, an increase in viscosity, the presence of water), but provide no direct insight into the chemical changes that have occurred (i.e. the breakdown of an additive package or loss of a specific chemical functionality). In many cases, detecting the chemical degradation is more useful for measuring the oil degradation accurately.

Most engine oils contain various additives to improve the performance of the base oil and slow down the degradation process. Engine oil is not only subject to continually high temperature conditions, but also continuous oxidized when the oil is contacted with water or air. Subsequently, the additives are also deteriorated. Accordingly, various degradation compounds and contaminants are accumulated in the oil. As a result, the viscosity increases, sludge is generated, and oxidized acid compounds easily corrode mechanical components.

Many attempts have been made to measure the quality of oil by various analysis methods. The total acid number measuring method, as described in ASTM (American Standard Test Method) D664, is one method for quantitatively analyzing oil. Other measuring methods also have been developed, such as the total alkali number measuring method (ASTM D4739), viscosity measuring method (ASTM D445/446), gas chromatography of diesel fuel diluents in used diesel engine oil (ASTM D3524-90), flash point measuring method (ASTM D92), oxidation measuring method (ASTM D2272), and so on. However, the above ASTM methods require extracting a sample of the oil from the mechanical device, e.g., the engine, and pre-treatment processes, involving much time and cost. Furthermore, the sample cannot be certain to really represent the status of the whole oil as used in the mechanical device.

Conventional oil analysis methods are usually based on analysis of physical and chemical characteristics of the oil, such as viscosity, dielectric constant, AC conductivity, resistance, impedance, corrosion, pH value, total alkali number, acid material content, spectrum analysis, optical density, and the like.

For example, a method for determining the viscosity of oil by measuring an acoustic transit time change and a phase shift in the oil is disclosed in U.S. Pat. No. 4,721,874 to Emmert. As the oil is oxidized, carboxyl-acid components are generated and the viscosity increases. However, this method has a serious disadvantage because viscosity cannot be measured correctly when the oil is diluted with low viscosity liquids, such as gasoline and water.

U.S. Pat. No. 5,929,754 discloses an engine oil deterioration sensor, which measures the dielectric constant of the oil. The dielectric constant of engine oil is typically between 1.6 and 3.2, depending upon the brand and the period of use. The dielectric constant increases with the period of use. Thus, the dielectric constant of engine oil provides an indication of the oil degradation. However, a mechanical failure, such as a damaged head gasket or a broken piston ring, will change the purity of the oil because contaminants, such as coolant (glycol ethylene), fuel, and water, can easily be introduced into the engine oil. Water and engine coolant have dielectric constants of approximately 87.5 and 37.0, respectively. The introduction of such contaminants into the engine oil significantly affects the measured dielectric constant of the engine oil.

U.S. Pat. No. 5,200,027 discloses a method for measuring the oil condition by using the difference between the conductivity of the oil and that of the contaminants in the oil. However, such a method may only be applied where the primary contaminant is an acid material or water.

U.S. Pat. No. 5,274,335 discloses a device for qualitatively determining the oil condition. The device is composed of two inert metal plated iron electrodes, for example gold plated, and the gap between the two electrodes is filled up with test engine oil. Since the electrical conductivity of engine oil, in general, is extremely low, the two electrodes have to be closely spaced to lower the ohmic resistance. In this device, this distance is set at 0.015 cm. A triangular waveform is applied to the electrodes with, for example, a maximum potential of 5 volts and a minimum potential of −5 volts. The output current increases gradually with the age or degradation of the engine oil. Since an oil's acid number will increase with use, the current increase may be associated to the electrochemical reaction involving the acidic decomposition products of engine oil. Therefore, the device can be used to monitor the oil condition and signal the need for an oil change. However, this method has a serious drawback in that the output current is greatly affected by fuel or coolant contaminants introduced into the oil, as well as the oil's acid number.

Molecular spectroscopy, such as a fourier transform infrared spectroscopy, is also widely used for analyzing the oil conditions. Molecular spectroscopy is based upon the phenomenon that a molecule absorbs the light energy of a specific frequency band, which is called the resonance frequency. By using this phenomenon, the existence of various materials in the oil, such as water, fuel, coolant (glycol ethylene), soot, additives, and so on, can be detected.

Infrared spectroscopy emits infrared light onto the oil sample in a cell and measures the amount of infrared light absorbed by the oil sample. An infrared spectrum is obtained by classifying the power of the infrared light passing through the oil sample by frequencies, thereby indicating which kinds of molecules exist in the oil sample. However, used engine oil commonly contains so many different molecules, additives, decomposition products, metallic wear particles, contaminants and the like, that a very complicated infrared spectrum is obtained. Thus, reliably analyzing the infrared spectrum and determining the kinds of molecules contained in the used oil are difficult.

Fluorescence spectroscopy is also used for measuring the degradation of engine oil. Generally, as the oxidation of the oil progresses, the power of the fluorescence increases.

In the case of car engine oil, aromatic hydrocarbons, polyphenyl hydrocarbons, and carboxyl compounds in the oil are known as organic fluorescent materials. Representative aromatic hydrocarbons include pylene, fluorene, etc.

Generally, mineral oil consists of iso-paraffin, naphthene, aromatic hydrocarbons, and naphtheno-aromatic hydrocarbon compounds. Aromatic hydrocarbons and naphtheno-aromatic hydrocarbon compounds have fluorescent effects due to benzene ring.

A synthetic base oil consists primarily of synthesized hydrocarbons, esters, ethers, halogenated compounds, and silicon polymers, and consists additionally of sodium potassium eutectics or inorganic polymers of boron, phosphorus and nitrogen. These most materials have fluorescent effects.

However, conventional fluorescence spectroscopy requires a considerably narrow oil sample path in order to minimize the light-darkening effect and expensive spectrum analyzing means. Thus, conventional fluorescence spectroscopy is not adapted for use in being mounted to a mechanical device, such as a car engine, and measuring oil degradation in real time. Also, contaminants in the oil tend to adhere to the surface of the oil sample path, thereby deteriorating the operational reliability.

Therefore, the each of the conventional methods used to measure oil oxidation levels have one or more drawbacks.

SUMMARY OF THE INVENTION

It is an object of the present invention to overcome the problems in the prior art and provide an apparatus for measuring oil oxidation capable of being mounted to mechanical devices and of detecting power of fluorescent light reflected from oil in real time as an indication of the oil oxidation.

Consistent with the foregoing object, and in accordance with the invention as embodied broadly described herein, an apparatus for measuring oil oxidation using fluorescent light reflected from oil is disclosed in one embodiment of the present invention, comprising a light-emitting means; a plurality of first light-transmitting means, which extend from the light-emitting means, for introducing light into oil at a plurality of different incident points; a plurality of light-reflecting means, which are immersed in the oil and disposed opposite the incident points, wherein each of the light-reflecting means is located at a different distance from the incident points; a plurality of second light-transmitting means, which extend from the incident points; a plurality of light-receiving means, which are connected to the second light-transmitting means, for receiving the light and generating signal outputs corresponding to the received light; and a control portion, which calculates a fluorescence quantum yield and a light absorption coefficient of the oil, based upon the signals from the light-receiving means, and compares the calculated fluorescence quantum yield and light absorption coefficient with reference fluorescence quantum yields and light absorption coefficients pre-stored in the control portion to determine the oil oxidation.

BRIEF DESCRIPTION OF DRAWINGS

The above object and features of the present invention will become more apparent from the following description of the preferred embodiments given in conjunction with the accompanying drawings. Understanding that these drawings depict only typical embodiments of the invention and are, therefore, not to be considered limiting of its scope, the invention will be described with additional specificity and detail through use of the accompanying drawings in which.

DETAILED DESCRIPTION OF THE PRESENT INVENTION

It will be readily understood that the components and steps of the present invention, as generally described and illustrated in the Figures herein and accompanying text, could be arranged and designed in a wide variety of different configurations while still utilizing the inventive concept. Thus, the following more detailed description of the preferred embodiments of the system and method of the present invention, as represented in FIGS. 1 through 5 and accompanying text, is not intended to limit the scope of the invention, as claimed, but it is merely representative of the presently preferred embodiments of the invention. The presently preferred embodiments of the invention will be best understood by reference to the drawings, wherein like parts or steps are designated by like numerals throughout.

When light passes through a medium, such as oil and the like, a certain amount of light is absorbed by the molecules of the medium and dispersed. This attenuation phenomenon of light is known to follows the Lambert-Beer's law.

$$P(x) = P_o e^{-\sigma x} \quad \text{Equation 1}$$

Here, $P_o$ means the power of the incident light, $P(x)$ is the power of the light after passing a distance x in the medium, and $\sigma$ refers to the light attenuation coefficient.

Generally, when the molecules or particles of the medium are negligibly small, the light is attenuated primarily by absorption. However, some materials, such as fluorophore, also radiate a certain amount of light during the light-absorbing process, which is indicated by a fluorescence quantum yield, $\alpha$. For example, if fluorophore absorbs incident light having of power $P_i$, the power $P_i'$ of the fluorescent light radiated from the fluorophore is defined as follows.

$$p_1' = \alpha P_i \quad \text{Equation 2}$$

If ultraviolet light of power $P_o$ is irradiated onto oil, since the power of the light passing a distance $x_i$ in the oil is calculated by above equation 1, the power $P(x)_i'$ of the fluorescent light radiated from the fluorophore at a distance of $x_i$ is defined as follows.

$$p(x)_1' = \alpha P(x_i) = \alpha P_o e^{-\alpha x_i} \quad \text{Equation 3}$$

When a molar concentration of the fluorophore in an oil is $C_1$, and the molar absorptivity of the fluorophore at an excitation wavelength band of $\lambda_o$ is $\beta_1$, above equation 3 is transformed into the following equation 4.

$$p(x)_1' = \alpha P_o e^{-(\beta_1 C_1) x_i} \quad \text{Equation 4}$$

When the light radiated from the fluorophore in the oil is absorbed at the excitation wavelength band of $\lambda (\lambda \neq \lambda_o, \lambda = \lambda_o \pm \Delta\lambda)$ while passing therethrough, the power of the fluorescent light passing a distance $x_i$ in the oil is defined as follows.

$$p_i(x) = p(x)_i' e^{-(\beta_2(\lambda)C_1) x_i} = \alpha(\lambda) P_o e^{-[(\beta_1 + \beta_2(\lambda))C_1] x_i} \quad \text{Equation 5}$$

Here, $\beta_2(\lambda)$ means the molar absorptivity of the fluorophore at the excitation wavelength band $\lambda$.

Figure 1:
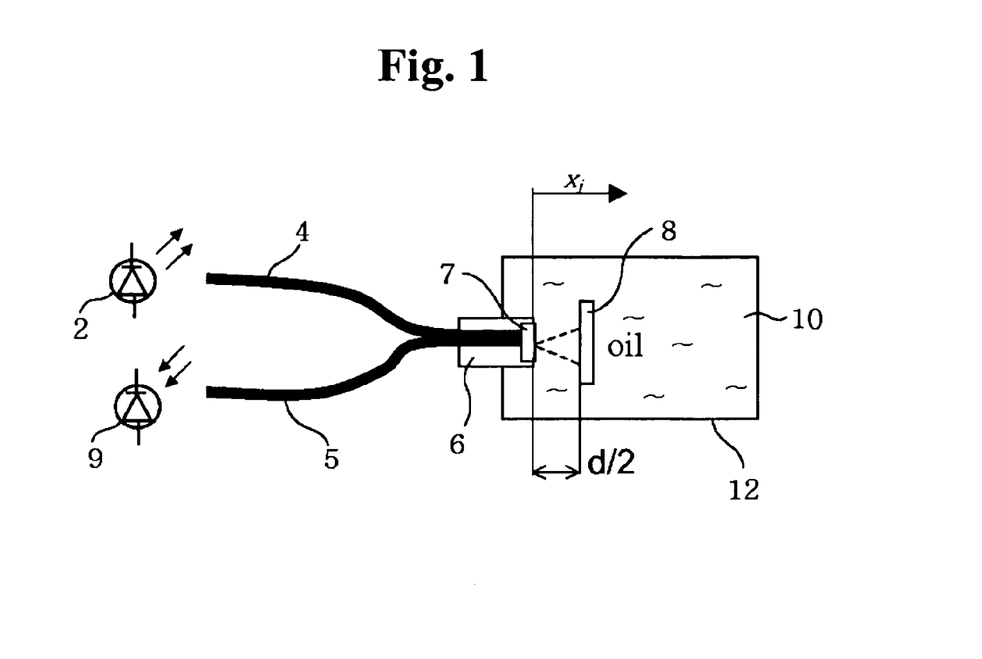
FIG. 1 is a perspective view of a light-detecting sensor used in an apparatus for measuring oil oxidation in accordance with a preferred embodiment of the present invention.

FIG. 1 shows schematically a preferred embodiment of a light-detecting sensor used in an apparatus for measuring oil oxidation in accordance with the present invention.

As shown in the drawing, ultraviolet light emitted from light-emitting means 2, e.g., an LED (light emitting diode), passes through first light-transmitting means 4, and is introduced into oil 10 via optical window 7. That is, optical window 7 is the incident point. Light-reflecting mirror 8 is mounted opposite to optical window 7, i.e., the incident point, by a distance of d/2. The light reflected from mirror 8 is transmitted to light-receiving means 9, e.g., a photoreceiver, via second light-transmitting means 5. Holder 6 is mounted to oil storage tank 12 for fixing the end portions of first and second light-transmitting means 4 and 5 and optical window 7. Preferably, the light-transmitting means is implemented as an optical fiber.

The power $P_F(\lambda)$ of the fluorescent light detected by light-receiving means 9 is derived from the following equation 6 by integrating the above equation 5.

$$P_F(\lambda) = \int_0^d p_i(x) dx \quad \text{Equation 6}$$
$$= \int_0^d \alpha P_o e^{-[(\beta_1 + \beta_2(\lambda))C_1 x_i]} dx$$
$$= \frac{\alpha P_o}{(\beta_1 + \beta_2(\lambda))C_1}(1 - e^{-((\beta_1 + \beta_2(\lambda))C_1 d)})$$
$$= \frac{\alpha(\lambda) P_o}{\beta(\lambda) C_1}(1 - e^{-\beta(\lambda)C_1 d})$$

Here, $\beta(\lambda)$ refers to $\beta_1 + \beta_2(\lambda)$, and $\beta(\lambda)C_1$ means the light absorption coefficient of the fluorophore existing in oil 10. The distance $x_i$, by which the light passes in oil 10, is d.

However, the output from light-receiving means 9 actually includes the power $P_F$ of the light from the fluorophore in oil 10 and the power of the light that is partly reflected from oil 10. Such power $P_R$ of the light reflected from non-fluorescence species in oil 10 is expressed as follows from the above equation 1.

$$P_R(\lambda) = P_o(\lambda) e^{-\beta'(\lambda)C'x} \quad \text{Equation 7}$$

Here, $\beta'(\lambda)$ refers to the molar absorptivity of the non-fluorescence species at the excitation wavelength band of $\lambda$ in oil 10, and C' means the molar concentration of the non-fluorescence species.

Accordingly, the total output from light-receiving means 9 is the sum of the power $P_F$ of the light reflected from the fluorophore and the power $P_R$ of the light from the non-fluorescence species, as in following equation 8.

$$P(\lambda) = P_F(\lambda) + P_R(\lambda) \quad \text{Equation 8}$$
$$= \frac{\alpha(\lambda) P_0(\lambda_0)}{\beta(\lambda) C_1}(1 - e^{-\beta(\lambda)C_1 x}) + P_0(\lambda) e^{-\beta'(\lambda)C'x}$$

The output from light-receiving means 9 depends upon the light-passing distance x in oil 10. If the light-passing distance x is relatively short, the output is dominated by the power $P_o$ of the light emitted from ultraviolet light emitting means 2. As the light-passing distance x increases, the output is determined primarily by the power $P_F$ of the fluorescent light.

Figure 2:
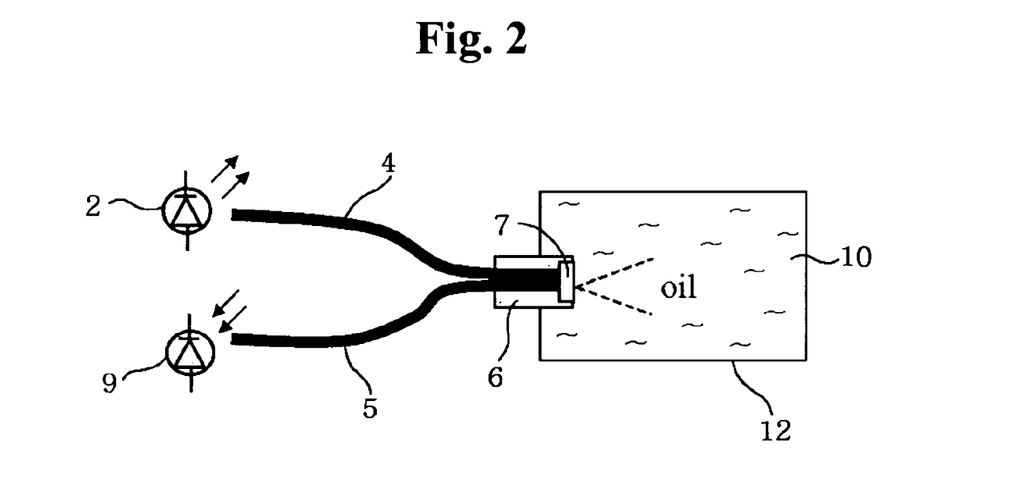
FIG. 2 is a perspective view of a light-detecting sensor used in an apparatus for measuring oil oxidation in accordance with a preferred embodiment of the present invention.

Now, referring to FIG. 2, which shows schematically another preferred embodiment of a light-detecting sensor used in an apparatus for measuring oil oxidation in accordance with the present invention, the light-detecting sensor has no light-reflecting mirror, in comparison with the previous embodiment shown in FIG. 1.

In the absence of a light-reflecting mirror, the light-passing distance x is the maximum ($x = x_{max}$) in oil 10, and above equation 5 is transformed into the equation 9 below.

$$p_i(\lambda) = \alpha(\lambda) P_o e^{-\beta(\lambda)C_1 x_{max}} \quad \text{Equation 9}$$

Thus, when the light-passing distance x has a maximum value $x_{max}$, the value of $P_i(\lambda)$ is minimized ($P_i(\lambda) = P_{min}(\lambda)$). From equation 9, $x_{max}$ is defined by the following equation 10.

$$x_{max} = -\frac{1}{\beta(\lambda)C_1} \ln \frac{p_{min}(\lambda)}{\alpha(\lambda) P_0} \quad \text{Equation 10}$$

The power $P_F(\lambda)$ of the fluorescent light at the maximum light-passing distance of $x_{max}$ is as follows.

$$P_F(\lambda) = \int_0^{x_{max}} p_i(\lambda) dx \quad \text{Equation 11}$$
$$= \int_0^{x_{max}} \alpha(\lambda) P_o e^{-\beta(\lambda)C_1 x} dx$$
$$= \frac{\alpha(\lambda) P_o}{\beta(\lambda) C_1}(1 - e^{-\beta(\lambda)C_1 x_{max}})$$
$$= \frac{\alpha(\lambda) P_o}{\beta(\lambda) C_1}\left(1 - \frac{p_{min}(\lambda)}{\alpha(\lambda) P_o}\right)$$
$$= \frac{\alpha(\lambda) P_o}{\beta(\lambda) C_1} - \frac{p_{min}(\lambda)}{\beta(\lambda) C_1}$$

Assuming that $p_{min}(\lambda)$ is close to zero, the power $P_F(\lambda)$ of the fluorescent light is expressed by the following equation 12.

$$P_F(\lambda) = \frac{\alpha(\lambda) P_o}{\beta(\lambda) C_1} \quad \text{Equation 12}$$

As known from equations 6 and 12, the power of $P_F(\lambda)$ of the fluorescent light is determined primarily by the fluorescence quantum yield $\alpha$, which increases as oil 10 is oxidized, and the light absorption coefficient $\beta(\lambda)C_1$. However, as the oil degrades, the oil darkens, and the attenuation of the light in the oil increases, thereby affecting the fluorescent light and decreasing the output from light-receiving means 9. Thus, in order to obtain an accurate measurement for oil oxidation, the influences of these phenomena should be considered together.

Figure 3:
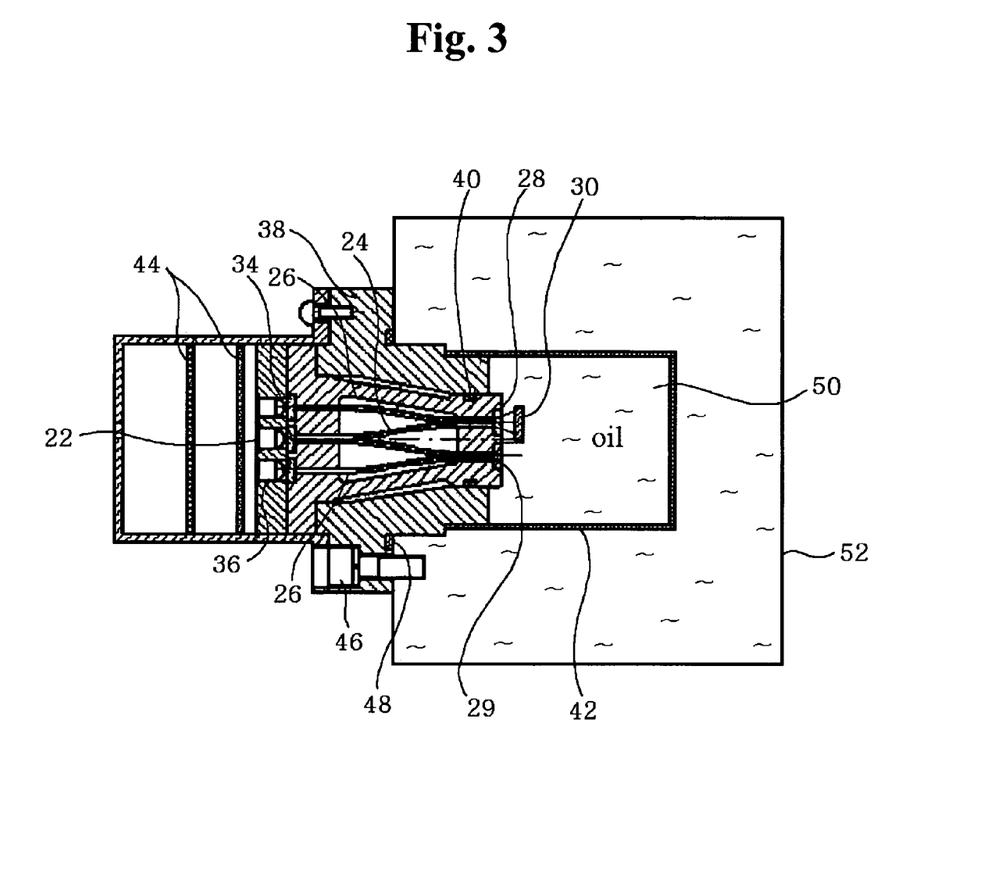
FIG. 3 is a cross-sectional view of an apparatus for measuring oil oxidation in accordance with a preferred embodiment of the present invention.
Figure 4:
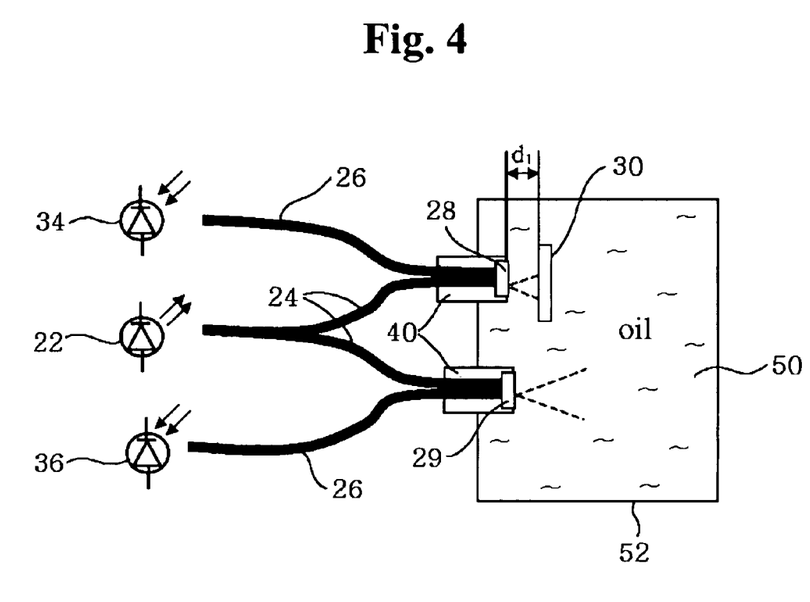
FIG. 4 is a schematic view showing the apparatus for measuring oil oxidation depicted in FIG. 3.

FIG. 3 is a cross-sectional view and FIG. 4 is a schematic view of an apparatus for measuring oil oxidation in accordance with a preferred embodiment of the present invention.

As shown in the drawings, an apparatus for measuring oil oxidation in accordance with a preferred embodiment of the present invention comprises ultraviolet light-emitting means 22, pair of first light-transmitting means 24, which are connected to light-emitting means 22 for introducing the ultraviolet light into oil 50 in oil tank 52, first optical window 28 and second optical window 29, to which pair of first light-transmitting means 24 are connected, respectively, pair of second light-transmitting means 26, which are connected to optical windows 28 and 29, respectively, and extend therefrom, and first light-receiving means 34 and second light-receiving means 36, which are connected to pair of second light-transmitting means 26, respectively, and receive the light reflected from oil 50. First and second optical windows 28 and 29 are light incident points. In addition, light-reflecting mirror 30 is immersed in oil 50 in oil tank 52, and is disposed opposite to first optical window 28, i.e., the incident point, by a distance of $d_1$.

Main body 38 for supporting the above-described structural components is mounted to oil tank 52 by means of a fastening means, e.g., screw 46. O-ring 48 is mounted between main body 38 and oil tank 52. Light-transmitting means 24 and 26 and optical windows 28 and 29 are fixed to main body 38 by means of holder 40. In order to prevent the surfaces of light-reflecting mirror 30 and optical windows 28 and 29 from being damaged by pollutants existing in oil 50, filter screen 42 is provided at main body 38 to surround light-reflecting mirror 30 and optical windows 28 and 29.

The signals from first light-receiving means 34 and second light-receiving means 36 are amplified by circuit board 44 and displayed on a monitor (not shown).

Preferably, ultraviolet light-emitting means 22 emits ultraviolet light having a wavelength of about 350~400 nm, and each light-transmitting means 24 or 26 is implemented as an optical fiber having a diameter of 1 mm and made from a polymer material.

As shown in FIG. 4, first light-receiving means 34 has a defined light-passing distance ($x=2d_1$). However, second light-receiving means 36 has an indefinite light-passing distance.

In case the light-passing distance x is indefinite ($x=x_{max}$), the power $P_R$ of the light from the non-fluorescence species in oil 50 is negligible. Accordingly, assuming that the light absorption coefficient $\beta C_1$ of the fluorophore in oil 50 equals the light absorption coefficient $\beta'C'$ of the non-fluorescence species ($\beta C_1 \approx \beta'C'$), the output $P_2$ from second light-receiving means 36 can be expressed in a more simple form. The output $P_1$ from first light-receiving means 34 and the output $P_2$ from second light-receiving means 36 can be expressed as follows, respectively, from the equations 8 and 12.

$$P_1(\lambda) = P_F(\lambda) + P_R(\lambda) \qquad \text{Equation 13}$$

$$= \frac{\alpha(\lambda)P_o}{\beta(\lambda)C_1}(1 - e^{-2\beta(\lambda)C_1 d_1}) + P_o(\lambda)e^{-2\beta(\lambda)C_1 d_1}$$

$$P_2(\lambda) = P_F(\lambda) + P_R(\lambda)(\to 0) \cong \frac{\alpha(\lambda)P_o}{\beta(\lambda)C_1} \qquad \text{Equation 14}$$

The light absorption coefficient $\beta$ and the fluorescence quantum yield $\alpha$ can be derived from equations 13 and 14, as follows.

$$\beta(\lambda) = \frac{\ln\left(\frac{P_0 - P_2}{P_1 - P_2}\right)}{2C_1 d_1} \qquad \text{Equation 15}$$

$$\alpha(\lambda) = \frac{P_2}{2d_1 P_0}\ln\left(\frac{P_0 - P_2}{P_1 - P_2}\right) \qquad \text{Equation 16}$$

Also, based on the outputs from first light-receiving means 34 and second light-receiving means 36, a control portion (not shown) calculates the fluorescence quantum yield $\alpha$ and the light absorption coefficient $\beta C_1$ of oil 50 from the following equations 17 and 18, and compares them with the pre-stored reference values of the fluorescence quantum yield and the light absorption coefficient, thereby determining the oil oxidation.

$$\alpha(\lambda) = \frac{U_2}{2d_1 U_0}\ln\left(\frac{U_0 - U_2}{U_1 - U_2}\right) \qquad \text{Equation 17}$$

$$\beta(\lambda)C_1 = \frac{\ln\left(\frac{U_0 - U_2}{U_1 - U_2}\right)}{2d_1} \qquad \text{Equation 18}$$

Here, $U_o$ means an output value (mV) of the power of light emitted from light-emitting means 22, which is pre-determined by the control portion. And, $U_1$ and $U_2$ are the output values (mV) from first light-receiving means 34 and second light-receiving means 36, respectively.

Figure 5:
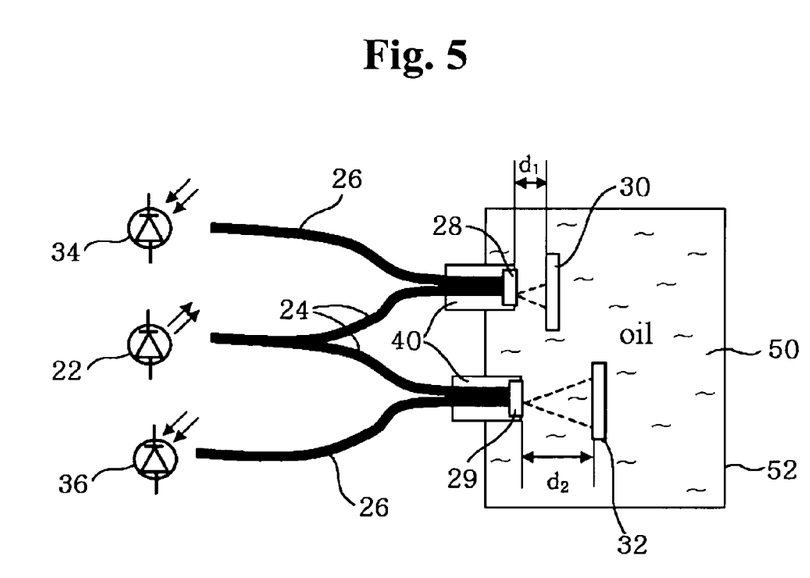
FIG. 5 is a schematic view showing an apparatus for measuring oil oxidation in accordance with a preferred embodiment of the present invention.

FIG. 5 shows schematically an apparatus for measuring oil oxidation in accordance with another preferred embodiment of the present invention.

As shown in the drawing, an apparatus for measuring oil oxidation of this embodiment further comprises one more light-reflecting mirror 32, which is immersed in oil 50 in oil tank 52 and disposed opposite to second optical window 29, i.e, the incident point, by a distance of $d_2$, in comparison with the apparatus of the previous embodiment.

In this structure, the output $P_1$ from first light-receiving means 34 having a light-passing distance of $2d_1$ and the output $P_2$ from second light-receiving means 36 having a light-passing distance of $2d_2$ are expressed as follows, respectively, from equation 8.

$$P_1(\lambda) = P_F(\lambda) + P_R(\lambda) \qquad \text{Equation 19}$$

$$= \frac{\alpha(\lambda)P_o}{\beta(\lambda)C_1}(1 - e^{-2\beta(\lambda)C_1 d_1}) + P_o(\lambda)e^{-2\beta'(\lambda)C' d_1}$$

$$P_2(\lambda) = P_F(\lambda) + P_R(\lambda) \qquad \text{Equation 20}$$

$$= \frac{\alpha(\lambda)P_o}{\beta(\lambda)C_1}(1 - e^{-2\beta(\lambda)C_1 d_2}) + P_o(\lambda)e^{-2\beta'(\lambda)C' d_2}$$

Assuming that the light absorption coefficient $\beta C_1$ of the fluorophore in oil 50 equals the light absorption coefficient β'C' of the non-fluorescence species (βC$_1$≈β'C'), equations 19 and 20 are transformed into following equations 21 and 22, respectively. From these, the control portion calculates the fluorescence quantum yield a and the light absorption coefficient βC$_1$ of oil 50, and compares them with the pre-stored reference values of the fluorescence quantum yield and the light absorption coefficient, thereby determining the oil oxidation.

$$U_1 = \frac{\alpha(\lambda)U_o}{\beta(\lambda)C_1}(1 - e^{-2\beta(\lambda)C_1 d_1}) + U_o e^{-2\beta(\lambda)C_1 d_1} \quad \text{Equation 21}$$

$$U_2 = \frac{\alpha(\lambda)U_o}{\beta(\lambda)C_1}(1 - e^{-2\beta(\lambda)C_1 d_2}) + U_o e^{-2\beta(\lambda)C_1 d_2} \quad \text{Equation 22}$$

The aforementioned apparatus for measuring oil oxidation according to the present invention has a composite structure of two types of light-detecting sensors, as depicted in FIGS. 1 and 2. However, the apparatus of the present invention may be structured with three or more sensors.

Hereinafter, test results of measuring the oxidation of mineral oil by using the apparatus in accordance with a preferred embodiment of the present invention will be described.

Gear oil having a viscosity of 468 (468 cSt) at a temperature of 40° C. was tested. The test was performed while varying the light-passing distance $d_i$ by 0, 0.4, 1.5, 2.3, 3.5, 4.3 and 5.5 mm, and indefinite ($d_i$=$x_{max}$). The test results are shown in the following table 1.

when the light-passing distance $d_i$ is indefinite ($d_i$=$x_{max}$). As the above results show, the mean fluorescence quantum yield $\alpha_{cl}$ of the clean oil is 0.054 mm$^{-1}$, and the mean fluorescence quantum yield $\alpha_{used}$ of the used oil is 0.065 mm$^{-1}$. The mean light absorption coefficient $\beta C_{cl}$ of the clean oil is 0.295 mm$^{-1}$, and the mean light absorption coefficient $\beta C_{used}$ of the used oil is 0.626 mm$^{-1}$.

Table 2 shows the mean values of the fluorescence quantum yield and the light absorption coefficient of the clean oil and the used oil, compared with the total acid numbers of the clean oil and the used oil measured by a conventional measuring method.

TABLE 2

| | Light absorption coefficient, βC (mm$^{-1}$) | Fluorescence quantum yield, α (mm$^{-1}$) | Total acid number (mgKOH/g) |
|---|---|---|---|
| Clean oil | 0.295 | 0.054 | 0.5 |
| Used oil | 0.626 | 0.065 | 1.18 |

As shown in table 2, the values of all the test items of used oil are larger than those of the clean oil.

Consequently, oil oxidation due to degradation can be measured by acquiring the fluorescence quantum yield $\alpha_{used}$ and the light absorption coefficient $\beta C_{used}$ of the used oil using the apparatus according to the present invention. In particular, the apparatus according to the present invention

TABLE 1

| Light-passing distance $d_i$ (mm) | Output value of clean oil, $U_{cl}$ (mV) | Fluorescence quantum yield of clean oil, $\alpha_{cl}$ (mm$^{-1}$) | Light absorption coefficient of clean oil, $\beta C_{cl}$ (mm$^{-1}$) | Output value of used oil, $U_{used}$ (mV) | Fluorescence quantum yield of used oil, $\alpha_{used}$ (mm$^{-1}$) | Light absorption coefficient of used oil, $\beta C_{used}$ (mm$^{-1}$) |
|---|---|---|---|---|---|---|
| 0 | 2012.0 | | | 2012.0 | | |
| 0.4 | 1613.5 | 0.063 | 0.346 | 1231.0 | 0.074 | 0.710 |
| 1.5 | 887.5 | 0.069 | 0.382 | 368.3 | 0.084 | 0.811 |
| 2.3 | 748.0 | 0.057 | 0.317 | 285.5 | 0.072 | 0.689 |
| 3.5 | 624.5 | 0.048 | 0.263 | 244.3 | 0.059 | 0.565 |
| 4.3 | 567.0 | 0.044 | 0.243 | 230.8 | 0.054 | 0.519 |
| 5.5 | 508.5 | 0.040 | 0.221 | 221.2 | 0.048 | 0.462 |
| mean value | | 0.054 | 0.295 | | 0.065 | 0.626 |
| $X_{max}$ | 364.0 | | | 210.0 | | |

The fluorescence quantum yield $\alpha^{cl}$ and $\alpha^{used}$ and the light absorption coefficient $\beta C_{cl}$ and $\beta C_{used}$ are derived from above equations 17 and 18, respectively, where $U_0$ is the output value of the power of light emitted from light-emitting means 22 ($d_i$=0), which is pre-determined by the control portion, $U_1$ is the output value from first light-receiving means 34 when the light-passing distance $d_i$ is varied by 0.4, 1.5, 2.3, 3.5, 4.3 and 5.5 mm, respectively, and $U_2$ is the output value from second light-receiving means 36, can effectively measure oil oxidation even under the darkened condition of degraded oil.

Next, test results of measuring the oxidation of synthetic oil using the apparatus according to the present invention will be described.

Poly alpha olefin gear oil having a viscosity of 300 (300 cSt) at a temperature of 40° C. was tested. The test was performed while varying the light-passing distance $d_i$ by 0, 2 and 4 mm, and indefinite ($d_i$=$x_{max}$). The results are shown in following Table 3.

TABLE 3

| Light-passing distance $d_i$ (mm) | Output value of clean oil, $U_{cl}$ (mV) | Fluorescence quantum yield of clean oil, $\alpha_{cl}$ (mm$^{-1}$) | Light absorption coefficient of clean oil, $\beta C_{cl}$ (mm$^{-1}$) | Output value of used oil, $U_{used}$ (mV) | Fluorescence quantum yield of used oil, $\alpha_{used}$ (mm$^{-1}$) | Light absorption coefficient of used oil, $\beta C_{used}$ (mm$^{-1}$) |
|---|---|---|---|---|---|---|
| 0 | 2137.8 | | | 2137.8 | | |
| 2 | 1962.5 | 0.002 | 0.023 | 1093.0 | 0.020 | 0.194 |
| 4 | 1801.0 | 0.002 | 0.023 | 513.0 | 0.024 | 0.230 |
| mean value | | 0.002 | 0.023 | | 0.022 | 0.212 |
| $X_{max}$ | 160.0 | | | 220.0 | | |

As also known from the table 3, the mean fluorescence quantum yield $\alpha_{used}$ of the used oil, which is 0.022 mm$^{-1}$, is larger than the mean fluorescence quantum yield $\alpha_{cl}$ of the clean oil, which is 0.002 mm$^{-1}$. And, the mean light absorption coefficient $\beta C_{used}$ of the used oil, which is 0.212 mm$^{-1}$, is larger than the mean light absorption coefficient $\beta C_{cl}$ of the clean oil, which is 0.023 mm$^{-1}$.

As described above in detail, the apparatus for measuring oil oxidation according to the present invention uses the phenomenon that the power of fluorescent light increases as oil is degraded. In particular, since the inventive apparatus includes two or more different types of light-detecting sensors, it can reliably measure the oil oxidation, although the oil darkens as the oil is degraded.

Further, a narrow oil sample path is unnecessary, so the apparatus of the present invention is simpler structure, and can be mounted to mechanical devices, such as a car engine, to measure the oil oxidation in real time.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the equivalent meaning and range of the claims are to be embraced within their scope.

What is claimed is:

1. An apparatus for measuring oil oxidation, comprising:
   a light-emitting means;
   a plurality of first light-transmitting means, which extend from the light-emitting means, for introducing light into oil at a plurality of different incident points;
   a plurality of light-reflecting means, which are immersed in the oil and disposed opposite the incident points, wherein each of the light-reflecting means is located at a different distance from the incident points;
   a plurality of second light-transmitting means, which extend from the incident points;
   a plurality of light-receiving means, which are connected to the second light-transmitting means, for receiving the light and generating signal outputs corresponding to the received light; and
   a control portion, which calculates a fluorescence quantum yield and a light absorption coefficient of the oil, based upon the signals from the light-receiving means, and compares the calculated fluorescence quantum yield and light absorption coefficient with reference fluorescence quantum yields and light absorption coefficients pre-stored in the control portion to determine the oil oxidation.

2. The apparatus for measuring oil oxidation of claim 1, wherein the light-transmitting means is an optical fiber.

3. The apparatus for measuring oil oxidation of claim 1, wherein the apparatus further comprises a filtering means, which surrounds the light-reflecting means and the incident points, for preventing the light-reflecting means and the incident points from being damaged by pollutants in the oil.

4. An apparatus for measuring oil oxidation, comprising:
   a light-emitting means;
   a pair of first optical fibers, which extend from the light-emitting means, for introducing light into oil at two different incident points;
   a light-reflecting mirror, which is immersed in the oil and disposed opposite one of the incident points and located at a predetermined light-passing distance from the incident point;
   a pair of second optical fibers, which extend from the two incident points, respectively;
   a first light-receiving means, which is connected to the second optical fiber extending from the incident point located opposite the light-reflecting mirror, for receiving the light and generating a signal output corresponding to the received light;
   a second light-receiving means, which is connected to the other second optical fiber for receiving the light and generating a signal output corresponding to the received light; and
   a control portion, which calculates a fluorescence quantum yield and a light absorption coefficient of the oil, based upon the signals from the first and second light-receiving means, and compares the calculated fluorescence quantum yield and light absorption coefficient with reference fluorescence quantum yields and light absorption coefficients pre-stored in the control portion to determine the oil oxidation.

5. The apparatus for measuring oil oxidation of claim 4, wherein the fluorescence quantum yield and the light absorption coefficient are calculated by the control portion from the following equations;

$$\alpha(\lambda) = \frac{U_2}{2d_1 U_0} \ln\left(\frac{U_0 - U_2}{U_1 - U_2}\right)$$

$$\beta(\lambda)C_1 = \frac{\ln\left(\frac{U_0 - U_2}{U_1 - U_2}\right)}{2d_1}$$

where, $\alpha(\lambda)$ is the fluorescence quantum yield, $d_1$ is the light-passing distance, $U_o$ is an output value of power of the light from light-emitting means, $U_1$ is an output value from the first light-receiving means, $U_2$ is an output value from the second light-receiving means, and $\beta(\lambda)C_1$ is the light absorption coefficient.

6. The apparatus for measuring oil oxidation of claim 4, wherein the apparatus further comprises a filtering means, which surrounds the light-reflecting mirror and the incident points, for protecting the light-reflecting mirror and the incident points from being damaged by pollutants in the oil.

7. An apparatus for measuring oil oxidation, comprising:
a light-emitting means;
a pair of first optical fibers, which extend from the light-emitting means, for introducing light into oil at two different incident points;
a first light-reflecting mirror and a second light-reflecting mirror, which are immersed in the oil and disposed opposite the two incident points, the first light-reflecting mirror and the second light-reflecting mirror being spaced apart from the two incidence points at different light-passing distances with respect to each other;
a pair of second optical fibers, which extend from the two incident points, respectively;
a first light-receiving means, which is connected to the second optical fiber extending from the incident point opposite to the first light-reflecting mirror, for receiving the light and generating a signal output corresponding to the received light;
a second light-receiving means, which is connected to the other second optical fiber extending from the incident point opposite to the second light-reflecting mirror, for receiving the light and generating a signal output corresponding to the received light; and
a control portion, which calculates a fluorescence quantum yield and a light absorption coefficient of the oil, based upon the signals from the first and second light-receiving means, and compares the calculated fluorescence quantum yield and light absorption coefficient with reference fluorescence quantum yields and light absorption coefficients pre-stored in the control portion to determine the oil oxidation.

8. The apparatus for measuring oil oxidation of claim 7, wherein the fluorescence quantum yield and the light absorption coefficient are calculated by the control portion from the following equations;

$$U_1 = \frac{\alpha(\lambda)U_0}{\beta(\lambda)C_1}(1 - e^{-2\beta(\lambda)C_1 d_1}) + U_0 e^{-2\beta(\lambda)C_1 d_1}$$

$$U_2 = \frac{\alpha(\lambda)U_0}{\beta(\lambda)C_1}(1 - e^{-2\beta(\lambda)C_1 d_2}) + U_0 e^{-2\beta(\lambda)C_1 d_2}$$

where, $d_1$ is the light-passing distance between the incidence point and the first light-reflecting mirror opposite thereto, $d_2$ is the light-passing distance between the incidence point and the second light-reflecting mirror opposite thereto, $U_0$ is an output value of power of the light from light-emitting means, $U_1$ is an output value from the first light-receiving means, $U_2$ is an output value from the second light-receiving means, $\alpha(\lambda)$ is the fluorescence quantum yield, and $\beta(\lambda)C_1$ is the light absorption coefficient.

9. The apparatus for measuring oil oxidation of claim 7, wherein the apparatus further comprises a filtering means, which surrounds the first light-reflecting mirror, the second light-reflecting mirror, and the incidence points, for protecting the first light-reflecting mirror, the second light-reflecting mirror, and the incidence points from being damaged by pollutants in the oil.

* * * * *